(12) United States Patent
Strobel et al.

(10) Patent No.: US 8,073,224 B2
(45) Date of Patent: Dec. 6, 2011

(54) SYSTEM AND METHOD FOR TWO-DIMENSIONAL VISUALIZATION OF TEMPORAL PHENOMENA AND THREE DIMENSIONAL VESSEL RECONSTRUCTION

(75) Inventors: Norbert Strobel, Heroldsbach (DE); Liron Yatziv, Plainsboro, NJ (US)

(73) Assignee: Siemens Aktiengesellschaft, München (DE)

( * ) Notice: Subject to any disclaimer, the term of this patent is extended or adjusted under 35 U.S.C. 154(b) by 820 days.

(21) Appl. No.: 12/168,199

(22) Filed: Jul. 7, 2008

(65) Prior Publication Data

US 2009/0016587 A1    Jan. 15, 2009

Related U.S. Application Data

(60) Provisional application No. 60/948,536, filed on Jul. 9, 2007.

(51) Int. Cl.
*G06K 9/00* (2006.01)

(52) U.S. Cl. ........................................ 382/130; 382/132

(58) Field of Classification Search .................. 382/128, 382/130–132; 378/98.12
See application file for complete search history.

(56) References Cited

U.S. PATENT DOCUMENTS

2011/0037761 A1* 2/2011 Mistretta et al. .............. 345/419

* cited by examiner

*Primary Examiner* — Jurie Yun
(74) *Attorney, Agent, or Firm* — Donald B. Paschburg; F. Chau & Associates, LLC

(57) ABSTRACT

A method for visualizing temporal phenomena and constructing 3D views from a series of medical images includes providing a first time series of digital images of contrast-enhanced blood flow in a patient, each acquired from a same viewing point with a known epipolar geometry, each said image comprising a plurality of intensities associated with an N-dimensional grid of points, calculating one or more time-density curves from said first time series of digital images, each curve indicative of how the intensity at corresponding points in successive images changes over time, and generating one or more overview images from said time density curves using a color coding technique, wherein said each overview image depict how a physical property value changes from said blood flow at selected corresponding points in said first time series of images.

28 Claims, 3 Drawing Sheets

SYSTEM AND METHOD FOR TWO-DIMENSIONAL VISUALIZATION OF TEMPORAL PHENOMENA AND THREE DIMENSIONAL VESSEL RECONSTRUCTION

CROSS REFERENCE TO RELATED UNITED STATES APPLICATIONS

This application claims priority from "Two-Dimensional Visualization of Temporal Phenomena and Three Dimensional Vessel Reconstruction from Few Views using Spatial and Temporal Constraints", U.S. Provisional Application No. 60/948,536 of Yatziv, et al, filed Jul. 9, 2007, the contents of which are herein incorporated by reference in their entirety.

TECHNICAL FIELD

This disclosure is directed to computing a 3D representation of a sparse (vascular) object from a limited number of views.

DISCUSSION OF THE RELATED ART

Blood flow rate and velocity information inside vasculature is important for the monitoring of endovascular treatments of arteriovenous malformations, diagnosis of vascular disease, and radio therapy treatment. Thus, the task of performing accurate and reliable assessment of instantaneous blood flow has been extensively researched. Out of many approaches, digital subtraction angiography has been found to have superior spatial-temporal resolution, is minimally invasive and readily available in the interventional suite. As a consequence, X-ray based videodensiometric blood flow techniques have become widely used. Of these algorithms, techniques involving bolus transport times are among the simplest to implement. Bolus refers to the administration of a medication, drug, contrast agent, or other compound that is given to raise blood concentration of the compound to an effective level. Bolus arrival times are typically determined by the analysis of time density curves, which plot local density at each pixel (or voxel) position, as a function of time. Bolus arrival times acquired from supplementary X-ray projections have also been used to fuse dynamic information with static 3D rotational angiography images to simultaneously provide morphological and functional information.

3-D reconstruction of vascular structures from X-ray images of two or more views based on a static contrast agent have also been extensively researched for coronary arterial tree reconstruction and other vascular structures. These methods include techniques involving placement of landmarks, predetermining the vessel shape, the use of models, interactive identification of matching structures, and rotational motion. Among all the proposed techniques, none has ever been applied to directly facilitate in-room clinical procedures for the whole vessel tree beyond some limited clinical trials, due to the large computational cost or inaccuracy of the reconstruction. Interestingly, while color coding of tissue areas based on time-density curves is common in perfusion computed tomography (CT), two-dimensional applications involving DSA sequences have not yet received much interest. One related work involves segmentation of vessel structures, but is limited to 2D visualization applications. When the multi-view geometry is known, 3-D reconstruction from two or more views is possible, if corresponding structures can be determined within common regions of interest.

SUMMARY OF THE INVENTION

Exemplary embodiments of the invention as described herein generally include methods and systems for fusing dynamic information with static 3D angiography images for 3D reconstruction using as few as two views taken in a bi-plane imaging geometry to simultaneously provide morphological and functional information. In additional to geometric (epipolar) constraints for the reconstruction of a 3D structure, such as a vessel tree, additional constraints include the use of a time varying physical process, such as contrast flow within vessels and temporal constraints, such as those derived from time-density curves, to resolve correspondence discrepancies. A method according to an embodiment of the invention can visualize the temporal behavior of sequences of registered data sets using advanced color coding techniques, in particular, summarizing two-dimensional DSA-sequences using one or more color-coded overview images. Further embodiments of the invention use the time dependence of contrast agent flow in blood vessels as a constraint for matching corresponding points between two images for the purpose of reconstruction, in addition to known epipolar constraints.

Methods according to embodiments of the invention are neither limited to 2D views nor to X-ray imaging, but can be applied to any multi-dimensional functional imaging technique, e.g., involving ultrasound or magnetic resonance imaging. In the first case, Doppler sonography may, for example, be used to derive functional information such as flow velocity. In the second case, different MR sequences may be used. In the case of bi-plane X-rays, one needs to observe the same physical process from multiple directions to reconstruct by triangulation, assuming that the correspondence between successive images can be determined.

According to an aspect of the invention, there is provided a method for visualizing temporal phenomena and constructing 3D views from a series of medical images, including providing a first time series of digital images of contrast-enhanced blood flow in a patient, each acquired from a same viewing point with a known epipolar geometry, each said image comprising a plurality of intensities associated with an N-dimensional grid of points, calculating one or more time-density curves from said first time series of digital images, each curve indicative of how the intensity at corresponding points in successive images changes over time, and generating one or more overview images from said time density curves using a color coding technique, wherein said each overview image depict how a physical property value changes from said blood flow at selected corresponding points in said first time series of images.

According to a further aspect of the invention, using a color coding technique comprises selecting a color space having at least 3 dimensions, associating a first of said 3 dimensions with time, associating a second of said 3 dimensions with said physical property value, and using a third of said 3 dimensions to blend in anatomical information.

According to a further aspect of the invention, the color space has 4 dimensions, wherein said fourth dimension is used to blend said overview image with one of said time series images.

According to a further aspect of the invention, the time series of digital images of blood flow comprises a digital subtraction angiography sequence of a contrast agent bolus propagating through said patient's bloodstream.

According to a further aspect of the invention, the method includes registering successive images in said time series of digital images.

According to a further aspect of the invention, the method includes providing a second time series of digital images of blood flow in said patient, said second time series acquired from a second viewing point with a known epipolar geometry, calculating one or more time-density curves from said second time series of digital images, each curve indicative of how the intensity at corresponding points in successive images changes over time, selecting a first projection point in a first image in one time series, applying spatial and temporal constraints to locate a corresponding second projection point in a temporally corresponding second image in the other time series, and calculating a 3D coordinate from the 2D coordinates of the first and second projection points.

According to a further aspect of the invention, applying spatial and temporal constraints comprises selecting a second point from the epipolar line in a temporally corresponding second image in the other time series, searching the time-density curves of each of the first and second points for a point where a time dependent feature value reaches an extreme value along at least one of the time-density curves, and calculating a correlation between the points on the time-density curves to determine a likelihood that said two points correspond to each other.

According to a further aspect of the invention, the method includes, for a selected image from said first time series of digital images, said selected image having an acquisition time, averaging corresponding images from said second time series of digital images that were acquired before and after the acquisition time of said selected image from said first time series of digital images.

According to a further aspect of the invention, the method includes calculating the 3-dimensional location of a plurality of selected points in a plurality of temporally corresponding images and constructing a 3-dimensional image of blood flow from said plurality of said 3-dimensional points.

According to a further aspect of the invention, the method includes estimating a flow velocity of said blood flow by selecting a start point in said 3-dimensional image of blood flow, an end point in said 3-dimensional image of blood flow, determining a flow arrival time at said start point and said end point, and calculating a vessel centerline distance from said 3-dimensional image of blood flow.

According to a further aspect of the invention, calculating a correlation between corresponding maximum points comprises imposing a size constraint on corresponding vessels encompassing said corresponding maximum points.

According to another aspect of the invention, there is provided a program storage device readable by a computer, tangibly embodying a program of instructions executable by the computer to perform the method steps for visualizing temporal phenomena and constructing 3D views from a series of medical images.

According to another aspect of the invention, there is provided a method for visualizing temporal phenomena and constructing 3D views from a series of medical images, said method comprising the steps of providing a first and a second time series of digital images of contrast enhanced blood flow in a patient, said first and second time series acquired from different viewing point, each with a known epipolar geometry, each said image comprising a plurality of intensities associated with an N-dimensional grid of points, calculating one or more time-density curves from said first and second time series of digital images, each curve indicative of how the intensity at corresponding points in successive images changes over time, selecting a first projection point in a first image in one time series, applying spatial and temporal constraints to locate a corresponding second projection point in a temporally corresponding second image in the other time series, and calculating a 3D coordinate from the 2D coordinates of the first and second projection points.

According to a further aspect of the invention, the method includes generating one or more overview images from said time density curves using a color coding technique, wherein said each overview image depict how a physical property value changes from said blood flow at selected corresponding points in said first time series of images, wherein using a color coding technique comprises selecting a color space having at least 3 dimensions, associating a first of said 3 dimensions with time, associating a second of said 3 dimensions with said physical property value, and using a third of said 3 dimensions to blend in anatomical information.

According to a further aspect of the invention, the method includes calculating the 3-dimensional location of a plurality of selected points in a plurality of temporally corresponding images and constructing a 3-dimensional image of blood flow from said plurality of said 3-dimensional points.

According to a further aspect of the invention, the time series of digital images of blood flow comprises a digital subtraction angiography sequence of a contrast agent bolus propagating through said patient's bloodstream.

According to a further aspect of the invention, the bolus is injected into each of several segments of a vessel tree, and further comprising constructing a 3-dimensional image of each segment individually, and combining said individual 3-dimensional segment images into a single 3-dimensional image of said vessel tree.

According to a further aspect of the invention, the method includes merging said 3-dimensional image of blood flow with said digital subtraction angiography sequence of images.

DETAILED DESCRIPTION OF EXEMPLARY EMBODIMENTS

Figure 1:
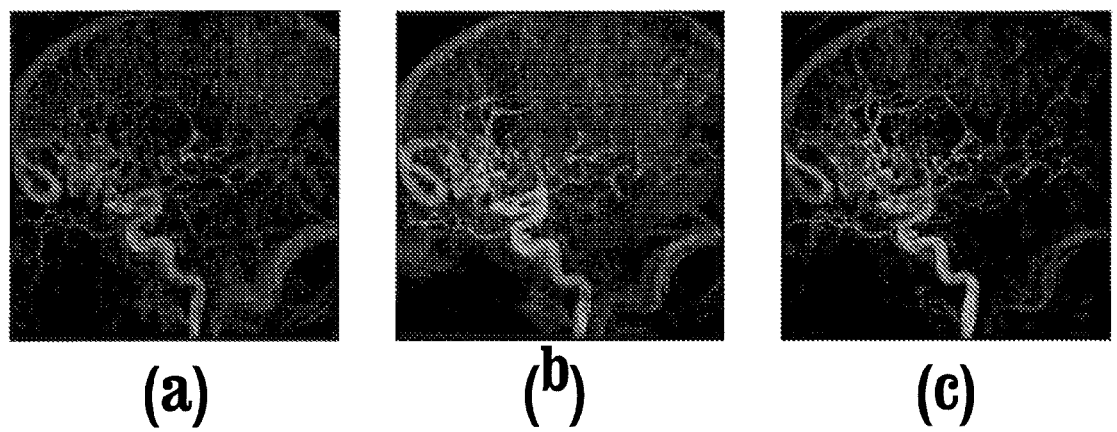
FIGS. 1(a)-(c) illustrate three time-density curve parameters, according to an embodiment of the invention.

Exemplary embodiments of the invention as described herein generally include systems and methods for computing a 3D representation of a sparse vascular object from a limited number of views. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

If frames recorded while acquiring a diagnostic imaging sequence are spatially registered, then changes in physical object properties at each fixed object location can be recorded over time. For example, if a contrast agent has been injected into some vascular structure, the temporal behavior of the contrast agent at each pixel or voxel, that is, the bolus arrival times, inside a certain field of view can be recorded using time-density curves. Time-density curves show how the intensity at each pixel location changes over time. In case of misregistration, for example due to patient motion, registration techniques can be applied to re-align corresponding pixel locations. Thus, from a sequence of registered images or volumes, one can generate overview images summarizing how physical properties change at each location, over time, using advanced color coding techniques. For example, bolus arrival times, derived from time-density curves of a sequence of X-ray images, can be summarized to illustrate how a contrast agent propagates from arteries to veins.

The use of enhanced color coding techniques can eliminate the need to explicitly segment blood vessels. Color coding can be based on color spaces or any color table. Color spaces known in the art include RGB (red, green, blue), CMY (cyan, magenta, yellow), HSV (hue, saturation, value), HSL (hue, saturation, luminance), YUV, YIQ, YdbDr, YPbPr and YCbCr. These last five color models are variations of one luma and two chroma dimensions models. In case of the HSV model, one can map a varying parameter range onto a Hue scale keeping Saturation and Value constant. On the Hue scale, each value corresponds to one color. For example, 0 is red, 45 is a shade of orange, and 240 corresponds to blue, on a scale from 0 to 360. For implementation, it is possible to convert from the HSV color space back to the RGB color space.

Depending on the application, one can also use Saturation and Value to encode a second and third parameter. If, for example, time-density curves are used to analyze bolus arrival times from a DSA sequence, then Hue is a parameter that may be used for encoding time. The Saturation parameter may be used to blend in anatomical background, such as bones, where a Saturation value of zero represents presence of bones and some other appropriate value their absence. According to an embodiment of the invention, this blending can be performed interactively. The Value parameter can used to represent the absolute or relative density change for the pixel. For example, selecting Value to represent the peak density value would emphasis the blood vessels. According to an embodiment of the invention, Value can be a non-linear function of peak density to emphasize blood vessels that are distant from the source of the contrast agent. According to other embodiments of the invention, a color table can be selected as well to map a parameter onto a customized range of colors. The example using the HSV color space is non-limiting, and it will be apparent to those skilled in the art how to use other color space coordinates to generate overview images summarizing how physical properties change at pixel locations over time.

According to another embodiment of the invention, an alpha channel, such as the opacity used for image compositing, can be used to help visualize and overlay the image onto other images and volumes. The alpha channel can also be used as a tool to visualize any parameter or just be set to have a linear correlation with Value. According to an embodiment of the invention, window-level techniques can be offered to help medical personal to better visualize different vessels. Interactive windowing may change any of the color coding parameters involved, linearly or non-linearly.

Many overview images using the aforementioned techniques may be generated, each summarizing the behavior of a different parameter. According to an embodiment of the invention, these parameters can be derived from the same underlying feature, such as a time-density curve. For example, bolus arrival time can be computed from a time-density curve using each of the following parameters:
  Time-of-peak opacification,
  Time-of-leading half-peak opacification,
  Time-of-trailing half-peak opacification,
  Time-of-a-single-opacification level,
  Downslope time differences,
  Time-of-peak-gradient arrival,
  Time-of-peak-negative-gradient arrival,
  Time-of-threshold density,
  Integral-corrected time (mean concentration time),
  Mean bolus arrival time,
  Time-of-level-of area under curve,
  Leading edge detection,
  Time-of-contrast arrival,
  Isodensity level transit time, and
  Cross-correlation of time-density curves, etc.
This list of parameters is exemplary and non-limiting, and other parameters as are known in the art may also be used to calculate a bolus arrival time.

FIGS. 1(a)-(c) illustrate three time-density curve parameters, according to an embodiment of the invention. FIG. 1(a) depicts time of contrast arrival, FIG. 1(b) depicts time-to-peak opacification, and FIG. 1(c) depicts time-of-clearance is depicted on the right. This last parameter is defined as the time to largest negative change in the time-density curve. For each of the figures, each color is associated with a particular point in time. Red depicts earlier time points (which highlight arteries) while shades of blue are associated with later points in time (highlighting veins).

As an example according to an embodiment of the invention, in a clinical 2D X-ray setup, a user may acquire a DSA sequence depicting how contrast flushes in and out of vasculature. This DSA sequence can then be used to compute time-density curves for selected sub-regions or for all pixels in the field of view. After selecting relevant bolus arrival time definitions most appropriate for the clinical application at hand, color (or even grayscale) composite overview images are generated as displayed in FIGS. 1(a)-(c). These images can be viewed by themselves or overlaid onto original images taken from the DSA sequence, such as the unopacified mask image, if anatomical clues, such as bone, are desired. Computed overview images can also serve as reference images for guiding fluoroscopic procedures. According to an embodiment of the invention, these overview images can be combined with anatomic X-ray projections, Overview images may be shown independent of each other, running as a movie or an animation. As an alternative, according to an embodiment of the invention, super-overviews can be generated by merging individual overviews, using image fusion techniques involving, for example, principal component analysis.

Many other medical quantities besides bolus arrival time and their relationship to each other can be derived from a sequence of registered multi-dimensional frames. Their change can be visually summarized using color coding techniques. The resulting overview images can be presented as a collection of single frames, a movie, or as a super-overview summarizing individual overviews that is generated using image fusion techniques.

When there are two or more X-ray images from two or more directions and the epipolar geometry is known, which means the cameras positions and parameters are known, one can calculate the 3D location of a point by finding corresponding points in each image. This process is known as triangulation or reconstruction. The challenging aspect is finding the corresponding points. One cannot in general say which vessel is which just by looking at the images. According to an embodiment of the invention, temporal constraints can be used in addition to the spatial, epipolar constraints to address the 3D reconstruction task from a limited number of views, e.g., from two views in the context of bi-plane imaging. For example, reconstructing brain vasculature in 3D together with functional information about blood flow from simultaneously acquired bi-plane views is useful, because it would only require that a patient holds still over the time for the DSA acquisition run. If there is patient motion, then motion correction algorithms can be applied to locally register successive views at the region of interest.

An embodiment of the invention provides a method to automatically find two matching points to address the correspondence between the different projections. According to an embodiment of the invention, time information is used to match points. One can apply the epipolar constraint and check among the time-density curves of pixels along the same epipolar line, which is a time-density constraint. Assuming there is no vessel overlap, when a point in one image reaches a maximum intensity, it should also reach maximum intensity in the other image. Those vessel pixel candidates whose time-density curves correlate best are most likely to match. In addition, the epipolar line constraint implies that the matching point must be on a single line on the other image. This leaves few options for matching and that is how points are matched. To further reduce the matching options, a method according to an embodiment of the invention not only looks at the maximum pixel intensity but also at maxima or minima of other time dependent features. For example, the maximum rate of change of intensity in time can be a second requirement for matching points.

One method according to an embodiment of the invention uses a normalized cross correlation to find a correlation between two vectors. The vectors in this case are the time-density curves, or a processed version of them, such as a denoised version using a median filter. For two points, each in one image, one can use the correlation in addition to the epipolar constraint to determine how likely they are to match each other. The point match could be done by simply picking the most likely candidate from the other image.

In reality, vessels do overlap, which makes it more challenging to match points. More sophisticated processes can be applied to handle these cases where there is vessel overlap, in which case the time-density curve may have more than one peak. One examples of such a process includes using a time-density curve model with respect to an estimated vessel width to more confidently match pixels (or small vessel segments) in the two projections. The model would be used as a filter to remove any time-density change caused due to an overlapping vessel of difference width. Another example would be to calculate the time-velocity or time-acceleration properties from the time-density curve on a pixel or small vessel segment, and use these properties with the normalizes cross-correlation to identify matches. In addition to the epipolar constraint and time-density-constraint, a size constraint may be applied, assuming that vessels are approximately piecewise circular/tubular structures. Examples of size constraints include restricting vessels to a predetermined maximum diameter, and ignoring vessels with a diameter less than another pre-determined value. The 3D reconstruction task can be further simplified by using selective hand injections from catheters into interesting vessels, such as potential Arteriovenous malformation (AVM) feeders, at a large zoom format to reduce vessel overlap. This way, the contrast agent injected from the catheter would reach the vessel of interest first which would make it stand out and ease correspondence task.

In addition, according to an embodiment of the invention, one can limit the number of views needed for 3D reconstruction by applying time windows. The simplest way to use a time window for 3D reconstruction from bi-plane views is to reconstruct one frame at a time, that is, using successive frames of a DSA sequence to grow a vessel tree from ground up. A practical approach would be to grow a vascular structure in 3D one frame at a time based on successive frames first and only to resort to normalized cross-correlation when it is needed to resolve ambiguities among overlapping vessel structures.

Bi-plane C-arm devices often interleave projections taken from the two views in real time due to bandwidth constraints. In other words, an A-plane view is followed by a B-plane view, and then another A-plane view starts that sequence again. If bi-plane views are not, however, acquired simultaneously, then a 3D reconstruction method needs to take into account the temporal lag between associated frames. As a result, for a 3D reconstruction from bi-plane views, according to an embodiment of the invention, an A-plane view can be combined with an associated average B-plane view created by summing B-plane projections obtained immediately before and after each A-plane view was acquired. According to another embodiment of the invention, an analogous technique can be applied to B-plane views that are paired up with temporally averaged A-plane views acquired immediately before and after. This idea can be extended to create new views using temporal interpolation techniques. This way, one may be able to increase an effective temporal resolution beyond the actual detector frame rate.

It is possible to independently inject contrast into each of the multiple segments of a vessel tree, reconstruct them individually, and put them all together. This would not only provide information about spatial and temporal properties of each vessel segment but also show how things are connected. If a patient does not move, each vessel segment frame remains registered with respect to the C-arm coordinate system. If the patient does move during the procedure, then a registration method can be applied to line up the individual vessel tree segments before putting them together.

Once there is have 3D information, one can estimate flow velocity. To this end, again using the example of bolus arrival times, the distance between a start point and an arrival point is needed together with bolus arrival time at these points. For example, the distance traveled along a 3D vessel centerline per frame interval provides an estimate of the instantaneous velocity of the contrast bolus. After the blood velocity is computed, it can be visualized using similar visualization and color coding techniques as described above.

One can merge any 3D structure reconstructed based on temporal and spatial consistency constraints with existing prior data sets, such as 3D Angio or DynaCT. The objective is to merge functional information associated with the vessel structure, such as that created by bi-plane reconstruction, with a static diagnostic image, such as a 3D Angio data set. Again, if the patient in question has not moved, then the data sets remain registered to any previously acquired 3D data set using the same (bi-plane) C-arm device. Manual or automatic registration methods can be used to rigidly or even non-rigidly register 3D structure or its projections with one another. For example, the registration could be performed using the computed vessel tree and angiograms from the DSA images. According to an embodiment of the invention, these can be acquired from both bi-plane views. Even without automatic registration, any reconstructed 3D vessel structure can always be projected and overlaid onto a fluoroscopic image and shifted by hand to account for patient movement.

Once a vessel tree has been reconstructed from bi-plane views, it can be used as a roadmap for guiding wires and catheters through vessels. If wires and catheters are seen under bi-plane, they can be reconstructed in 3D as well. Special 3D visualization effects can be used to view the catheter or guidewire embedded in a 3D reconstructed structure or a pre-acquired 3D volume, such as a chase view.

Figure 2:
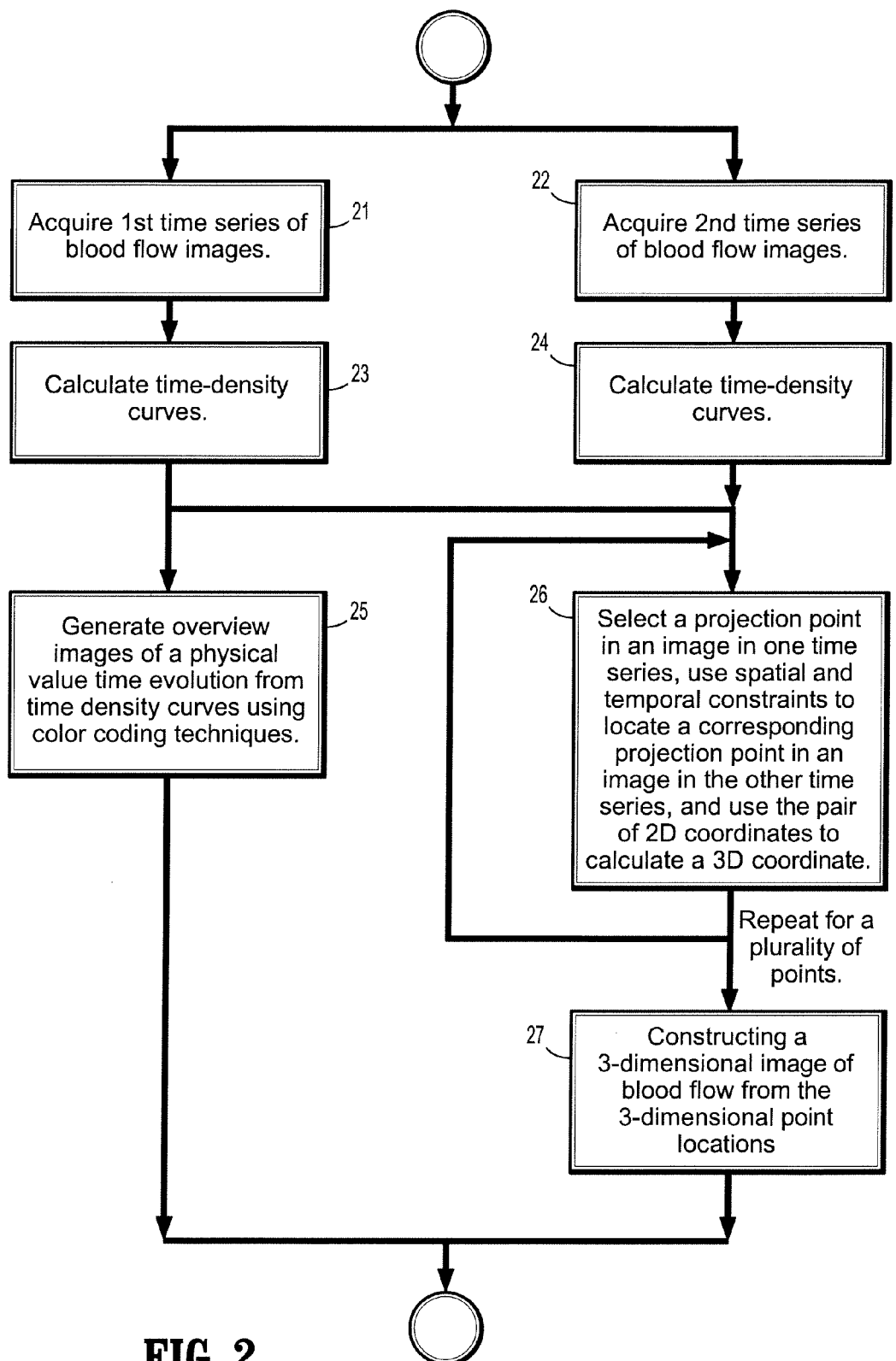
FIG. 2 is a flowchart of a method for computing a 3D representation of a sparse vascular object from a limited number of views, according to an embodiment of the invention.

A flowchart of a method according to an embodiment of the invention for two-dimensional visualization of temporal phenomena and three dimensional vessel reconstruction is presented in FIG. 2. Referring now to the figure, a method starts by providing at step 21 a first time series of digital images of blood flow in a patient. The images in this first time series are each acquired from the same viewing point and have a known epipolar geometry. At step 23, one or more time-density curves are calculated from the first time series of images. As described above, the time-density curves illustrate how the intensity at corresponding points in successive images changes over time. At step 22, a second time series of digital images of blood flow in the patient are provided. This second time series of images are acquired from a different viewing point and also have a known epipolar geometry. These time series could be acquired from different bi-plane C-arm apparatuses. As with the first time series, at step 24, one or more time-density curves are calculated from the series time series of images. At step 25, one or more overview images is generated from one of the sets of time density curves using a color coding technique as described above, wherein the overview images depict how a physical property value changes according to the blood flow at selected corresponding points in the series of images.

At step 26, a projection point in an image in one time series is selected, spatial and temporal constraints are used to locate a corresponding projection point in a temporally corresponding image in the other time series, and the pair of 2D coordinates is used to calculate a 3D coordinate from the two 2D projection coordinates. A temporally corresponding image is an image acquired substantially simultaneously with the other image. If the image in the second time series was not acquired simultaneously with the image from the first time series, for one of the time series, one can compute an average of images acquired before and after the acquisition time of the image in the other time series, as described above. Applying the spatial and temporal constraints involves selecting a first point in one of the first and second digital images, and then selecting a second point from the epipolar line in the other of said first and second digital images. This is the application of the spatial constraint. Applying the temporal constraint then involves searching the time-density curves of each of the first and second points for a point where a time dependent feature value, such as the image point intensity, reaches an extreme value along at least one of the time-density curves. Another non-limiting time dependent feature that can be used is the maximum rate of change of intensity in time. If there is no vessel overlap, there should be an extreme value for the other feature value. Then, a correlation between the corresponding points on the time-density curves is calculated by any of the methods described above to determine a likelihood that said two points correspond to each other. Step 26 can be repeated fro a plurality of points. At step 27, a 3D image is constructed from a plurality of 3D coordinates.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 3:
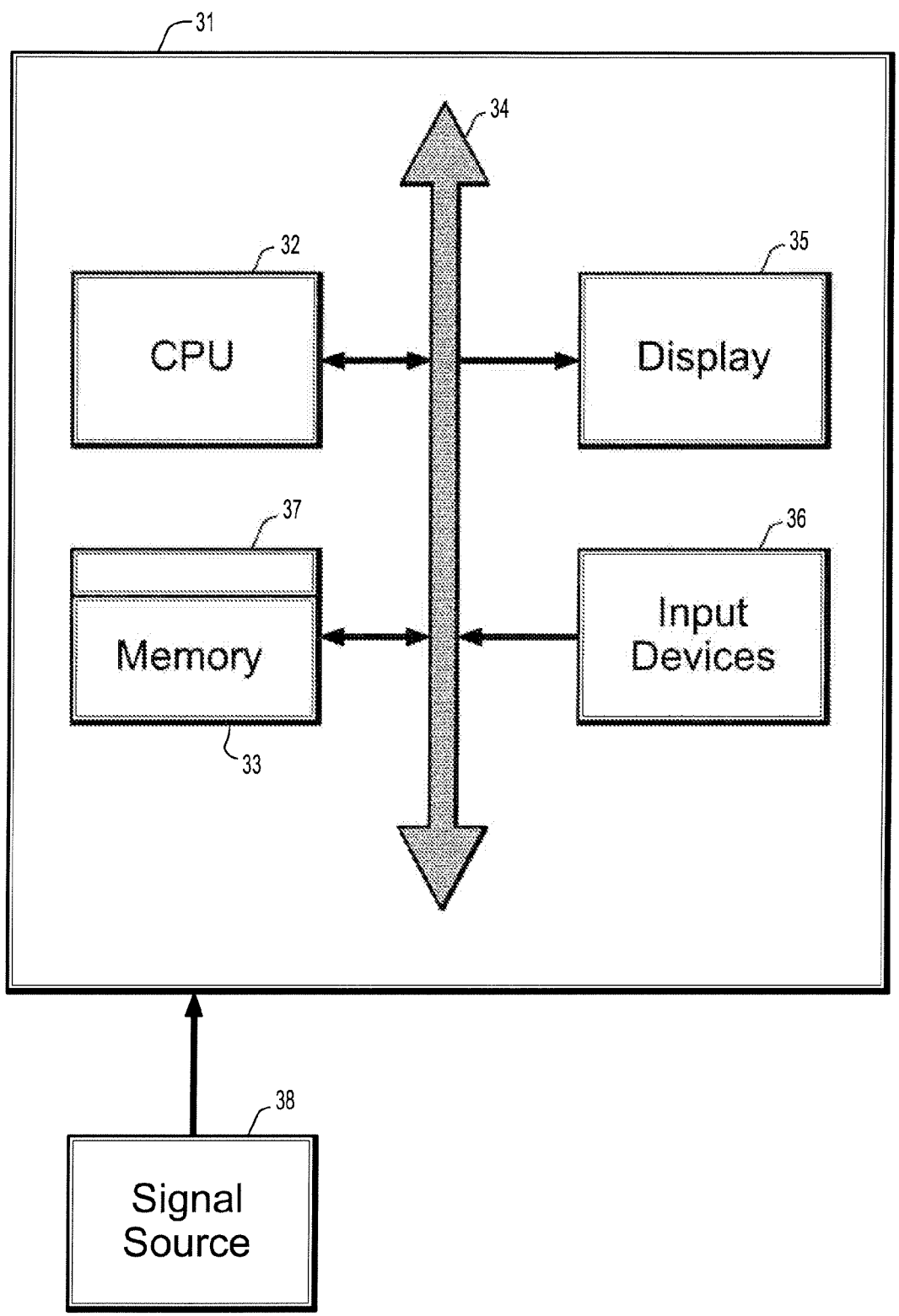
FIG. 3 is a block diagram of an exemplary computer system for implementing a method for computing a 3D representation of a sparse vascular object from a limited number of views, according to an embodiment of the invention.

FIG. 3 is a block diagram of an exemplary computer system for implementing a method for computing a 3D representation of a sparse vascular object from a limited number of views, according to an embodiment of the invention. Referring now to FIG. 3, a computer system 31 for implementing the present invention can comprise, inter alia, a central processing unit (CPU) 32, a memory 33 and an input/output (I/O) interface 34. The computer system 31 is generally coupled through the I/O interface 34 to a display 35 and various input devices 36 such as a mouse and a keyboard. The support circuits can include circuits such as cache, power supplies, clock circuits, and a communication bus. The memory 33 can include random access memory (RAM), read only memory (ROM), disk drive, tape drive, etc., or a combinations thereof. The present invention can be implemented as a routine 37 that is stored in memory 33 and executed by the CPU 32 to process the signal from the signal source 38. As such, the computer system 31 is a general purpose computer system that becomes a specific purpose computer system when executing the routine 37 of the present invention.

The computer system 31 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:
1. A method for visualizing temporal phenomena and constructing 3D views from a series of medical images, said method comprising the steps of:
providing a first time series of digital images of contrast-enhanced blood flow in a patient, each acquired from a same viewing point with a known epipolar geometry, each said image comprising a plurality of intensities associated with an N-dimensional grid of points;

calculating one or more time-density curves from said first time series of digital images, each curve indicative of how the intensity at corresponding points in successive images changes over time; and generating one or more overview images from said time density curves using a color coding technique, wherein each of said one or more overview images depict how a physical property value changes from said blood flow at selected corresponding points in said first time series of images.

2. The method of claim 1, wherein using a color coding technique comprises selecting a color space having at least 3 dimensions, associating a first of said 3 dimensions with time, associating a second of said 3 dimensions with said physical property value, and using a third of said 3 dimensions to blend in anatomical information.

3. The method of claim 2, wherein said color space has 4 dimensions, wherein said fourth dimension is used to blend said overview image with one of said time series images.

4. The method of claim 1, wherein said time series of digital images of blood flow comprises a digital subtraction angiography sequence of a contrast agent bolus propagating through said patient's bloodstream.

5. The method of claim 1, further comprising registering successive images in said time series of digital images.

6. The method of claim 1, further comprising:

providing a second time series of digital images of blood flow in said patient, said second time series acquired from a second viewing point with a known epipolar geometry;

calculating one or more time-density curves from said second time series of digital images, each curve indicative of how the intensity at corresponding points in successive images changes over time;

selecting a first projection point in a first image in one time series;

applying spatial and temporal constraints to locate a corresponding second projection point in a temporally corresponding second image in the other time series; and calculating a 3D coordinate from the 2D coordinates of the first and second projection points.

7. The method of claim 6, wherein applying spatial and temporal constraints comprises:

selecting a second point from an epipolar line in a temporally corresponding second image in the other time series;

searching the time-density curves of each of the first and second points for a point where a time dependent feature value reaches an extreme value along at least one of the time-density curves; and calculating a correlation between the points on the time-density curves to determine a likelihood that said two points correspond to each other.

8. The method of claim 6, further comprising, for a selected image from said first time series of digital images, said selected image having an acquisition time, averaging corresponding images from said second time series of digital images that were acquired before and after the acquisition time of said selected image from said first time series of digital images.

9. The method of claim 6, further comprising calculating the 3-dimensional location of a plurality of selected points in a plurality of temporally corresponding images and constructing a 3-dimensional image of blood flow from said plurality of said 3-dimensional points.

10. The method of claim 9, further comprising estimating a flow velocity of said blood flow by selecting a start point in said 3-dimensional image of blood flow, an end point in said 3-dimensional image of blood flow, determining a flow arrival time at said start point and said end point, and calculating a vessel centerline distance from said 3-dimensional image of blood flow.

11. The method of claim 7, wherein calculating a correlation between points comprises imposing a size constraint on corresponding vessels encompassing said corresponding maximum points.

12. A method for visualizing temporal phenomena and constructing 3D views from a series of medical images, said method comprising the steps of:

providing a first and a second time series of digital images of contrast enhanced blood flow in a patient, said first and second time series acquired from different viewing point, each with a known epipolar geometry, each said image comprising a plurality of intensities associated with an N-dimensional grid of points;

calculating one or more time-density curves from said first and second time series of digital images, each curve indicative of how the intensity at corresponding points in successive images changes over time;

selecting a first projection point in a first image in one time series;

applying spatial and temporal constraints to locate a corresponding second projection point in a temporally corresponding second image in the other time series; and calculating a 3D coordinate from the 2D coordinates of the first and second projection points.

13. The method of claim 12, further comprising generating one or more overview images from said time density curves using a color coding technique, wherein each of said one or more overview images depict how a physical property value changes from said blood flow at selected corresponding points in said first time series of images, wherein using a color coding technique comprises selecting a color space having at least 3 dimensions, associating a first of said 3 dimensions with time, associating a second of said 3 dimensions with said physical property value, and using a third of said 3 dimensions to blend in anatomical information.

14. The method of claim 12, further comprising calculating the 3-dimensional location of a plurality of selected points in a plurality of temporally corresponding images and constructing a 3-dimensional image of blood flow from said plurality of said 3-dimensional points.

15. The method of claim 14, wherein said time series of digital images of blood flow comprise a digital subtraction angiography sequence of a contrast agent bolus propagating through said patient's bloodstream.

16. The method of claim 15, wherein said bolus is injected into each of several segments of a vessel tree, and further comprising constructing a 3-dimensional image of each segment individually, and combining said individual 3-dimensional segment images into a single 3-dimensional image of said vessel tree.

17. The method of claim 15, further comprising merging said 3-dimensional image of blood flow with said digital subtraction angiography sequence of images.

18. A non-transitory computer readable program storage device readable by a computer, tangibly embodying a program of instructions executable by the computer to perform the method steps for visualizing temporal phenomena and constructing 3D views from a series of medical images, said method comprising the steps of:

providing a first time series of digital images of contrast-enhanced blood flow in a patient, each acquired from a same viewing point with a known epipolar geometry, each said image comprising a plurality of intensities associated with an N-dimensional grid of points;

calculating one or more time-density curves from said first time series of digital images, each curve indicative of how the intensity at corresponding points in successive images changes over time; and generating one or more overview images from said time density curves using a color coding technique, wherein each of said one or more overview images depict how a physical property value changes from said blood flow at selected corresponding points in said first time series of images.

19. The non-transitory computer readable program storage device of claim 18, wherein using a color coding technique comprises selecting a color space having at least 3 dimensions, associating a first of said 3 dimensions with time, associating a second of said 3 dimensions with said physical property value, and using a third of said 3 dimensions to blend in anatomical information.

20. The non-transitory computer readable program storage device of claim 19, wherein said color space has 4 dimensions, wherein said fourth dimension is used to blend said overview image with one of said time series images.

21. The non-transitory computer readable program storage device of claim 18, wherein said time series of digital images of blood flow comprises a digital subtraction angiography sequence of a contrast agent bolus propagating through said patient's bloodstream.

22. The non-transitory computer readable program storage device of claim 18, the method further comprising registering successive images in said time series of digital images.

23. The non-transitory computer readable program storage device of claim 18, the method further comprising:
providing a second time series of digital images of blood flow in said patient, said second time series acquired from a second viewing point with a known epipolar geometry;

calculating one or more time-density curves from said second time series of digital images, each curve indicative of how the intensity at corresponding points in successive images changes over time;

selecting a first projection point in a first image in one time series;

applying spatial and temporal constraints to locate a corresponding second projection point in a temporally corresponding second image in the other time series; and calculating a 3D coordinate from the 2D coordinates of the first and second projection points.

24. The non-transitory computer readable program storage device of claim 23, wherein applying spatial and temporal constraints comprises:
selecting a second point from an epipolar line in a temporally corresponding second image in the other time series;

searching the time-density curves of each of the first and second points for a point where a time dependent feature value reaches an extreme value along at least one of the time-density curves; and calculating a correlation between the points on the time-density curves to determine a likelihood that said two points correspond to each other.

25. The non-transitory computer readable program storage device of claim 23, the method further comprising, for a selected image from said first time series of digital images, said selected image having an acquisition time, averaging corresponding images from said second time series of digital images that were acquired before and after the acquisition time of said selected image from said first time series of digital images.

26. The non-transitory computer readable program storage device of claim 23, the method further comprising calculating the 3-dimensional location of a plurality of selected points in a plurality of temporally corresponding images and constructing a 3-dimensional image of blood flow from said plurality of said 3-dimensional points.

27. The non-transitory computer readable program storage device of claim 26, the method further comprising estimating a flow velocity of said blood flow by selecting a start point in said 3-dimensional image of blood flow, an end point in said 3-dimensional image of blood flow, determining a flow arrival time at said start point and said end point, and calculating a vessel centerline distance from said 3-dimensional image of blood flow.

28. The non-transitory computer readable program storage device of claim 24, wherein calculating a correlation between points comprises imposing a size constraint on corresponding vessels encompassing said corresponding maximum points.

* * * * *